(12) United States Patent
Bourlion et al.

(10) Patent No.: US 8,419,746 B2
(45) Date of Patent: Apr. 16, 2013

(54) EXPLORATION DEVICE TO MONITOR THE PENETRATION OF AN INSTRUMENT IN AN ANATOMIC STRUCTURE

(75) Inventors: Maurice Bourlion, Saint-Chamond (FR); Dominique Petit, Verton (FR); Gérard Vanacker, Saint-Maur (FR)

(73) Assignee: SpineGuard (FR)

( * ) Notice: Subject to any disclaimer, the term of this patent is extended or adjusted under 35 U.S.C. 154(b) by 1116 days.

(21) Appl. No.: 10/589,182

(22) PCT Filed: Feb. 11, 2005
(Under 37 CFR 1.47)

(86) PCT No.: PCT/FR2005/000338
§ 371 (c)(1),
(2), (4) Date: Oct. 11, 2007

(87) PCT Pub. No.: WO2005/077282
PCT Pub. Date: Aug. 25, 2005

(65) Prior Publication Data
US 2008/0167659 A1  Jul. 10, 2008

(30) Foreign Application Priority Data
Feb. 11, 2004 (FR) ..................... 04 01361

(51) Int. Cl.
*A61B 17/56* (2006.01)
(52) U.S. Cl.
USPC .......................................................... 606/102
(58) Field of Classification Search .................. 606/102, 606/506, 547, 86 R; 604/117
See application file for complete search history.

(56) References Cited

U.S. PATENT DOCUMENTS

| | | | | |
|---|---|---|---|---|
| 5,353,802 A | * | 10/1994 | Ollmar | 600/547 |
| 5,861,002 A | * | 1/1999 | Desai | 606/210 |
| 6,391,005 B1 | * | 5/2002 | Lum et al. | 604/117 |
| 6,706,016 B2 | * | 3/2004 | Cory et al. | 604/117 |
| 6,847,841 B1 | * | 1/2005 | El Hatw | 600/547 |
| 6,951,549 B1 | * | 10/2005 | Beyerlein | 604/117 |
| 7,416,552 B2 | * | 8/2008 | Paul et al. | 606/41 |
| 7,563,232 B2 | * | 7/2009 | Freeman et al. | 600/583 |
| 7,580,743 B2 | * | 8/2009 | Bourlion et al. | 600/547 |
| 7,780,631 B2 | * | 8/2010 | Lum et al. | 604/117 |
| 8,092,457 B2 | * | 1/2012 | Oettinger et al. | 606/80 |
| 8,241,229 B2 | * | 8/2012 | Herndon | 600/583 |
| 2002/0008526 A1 | * | 1/2002 | Martin et al. | 324/678 |
| 2003/0088186 A1 | * | 5/2003 | Doody | 600/547 |

FOREIGN PATENT DOCUMENTS

FR          2 835 732 A1    8/2003

* cited by examiner

*Primary Examiner* — Kevin T Truong
*Assistant Examiner* — Christopher Beccia
(74) *Attorney, Agent, or Firm* — DLA Piper LLP (US)

(57) ABSTRACT

An exploration device to monitor the penetration of an instrument in an anatomic structure including at least two electrodes; a source of voltage supplying the at least two electrodes; a means for measuring impedance between the electrodes; a means of angular location formed by at least one electrode punctually coinciding with a peripheral surface of the penetration instrument, the coinciding surface of the electrode having a position set off from a longitudinal axis the instrument; and means for detecting a position of the at least one electrode.

19 Claims, 4 Drawing Sheets

EXPLORATION DEVICE TO MONITOR THE PENETRATION OF AN INSTRUMENT IN AN ANATOMIC STRUCTURE

RELATED APPLICATION

This is a §371 of International Application No. PCT/FR2005/000338, with an international filing date of Feb. 11, 2005 (WO 2005/077282 A1, published Aug. 25, 2005), which is based on French Patent Application No. 04/01361, filed Feb. 11, 2004.

TECHNICAL FIELD

This invention refers to the field of spinal surgery.

BACKGROUND

In surgery of the spine, for example, for pedicular drilling, the bone cortex is often crossed, broken or damaged by the drilling instrument, that may then lead to poor positioning of the pedicular screws. Following this poor positioning, the pedicular screws, inducing pain, paralysis, haemorrhage, etc. in the patient, may require another surgical intervention or, in certain cases, cause irreparable damage.

FR 2 835 732 discloses a device to monitor penetration of an instrument (drill or other type of instrument) in the vertebra by measuring the differences in the electrical impedance during penetration so that the practitioner is constantly aware whether the end of the instrument is leaving the bone cortex and penetrating into a zone of soft tissue (marrow, nerves, tissue). In that case, the practitioner modifies the path of the penetration instrument to return to the bone cortex.

Such a device may also be used to detect the formation of a gap in the bone cortex during drilling.

To facilitate repositioning of the penetration instrument during a drilling operation (or similar type of operation such as tapping, boring, etc.), but also to enable proper positioning of the pedicular screw or any other surgical instrument, the practitioner has to know the exact position of the gaps formed during the drilling.

It could therefore be advantageous to provide an exploration device indicating the position of the gaps formed during a drilling (or similar) operation.

SUMMARY

This invention relates to an exploration device to monitor the penetration of an instrument in an anatomic structure including at least two electrodes, a source of voltage supplying the at least two electrodes, a means for measuring impedance between the electrodes, a means of angular location formed by at least one electrode punctually coinciding with a peripheral surface of the penetration instrument, the coinciding surface of the electrode having a position set off from a longitudinal axis of the instrument, and means for detecting a position of the at least one electrode.

BRIEF DESCRIPTION OF THE DRAWINGS

Selected, representative aspects will be better understood using the following description that is only provided for explanatory purposes, with reference to the appended figures.

DETAILED DESCRIPTION

We disclose exploration devices to monitor penetration of an instrument in an anatomic structure, in particular bone structure, comprising a source of voltage supplying at least two electrodes and a means to measure the impedance between the electrodes. The device includes a means of angular location formed by at least one electrode punctually coinciding with a peripheral surface of the penetration instrument, the coinciding surface of the electrode whose position is set off from the longitudinal axis of the instrument, as well as a means to detect the position of the electrode.

By "punctual coincidence" and "punctually coinciding," we mean a contact surface partially and discontinually coinciding with the peripheral surface of the aforementioned penetration instrument. In particular, an annular contact surface, and by extension a tubular shape are not considered as providing punctual coincidence.

Depending on whether one desires taking lateral readings or readings at the end of the penetration instrument or laterally and at the end, respectively, the penetration instrument may be equipped with at least one electrode coinciding with the lateral surface of the penetration instrument and/or at least one electrode coinciding with the peripheral surface of the distal end of the penetration instrument.

Advantageously, the coinciding electrode is driven in rotation, the coinciding electrode being driven at speed of rotation so that it sweeps at least 360 degrees per level of insertion of the penetration instrument in the bone structure.

The device may comprise a plurality of angularly spaced coinciding fixed electrodes and the means to measure the impedance delivers a signal corresponding to each of the electrodes.

The electrodes may consist of punctual contacts longitudinally and angularly spaced out.

The electrodes may be formed by longitudinal strips.

According to one selected configuration, the electrodes are distributed around the longitudinal axis of the penetration instrument.

The electrodes may be symmetrically arranged with respect to the longitudinal axis of the penetration instrument.

The electrodes may consist of conducting rods of circular, semi-annular, rectangular and/or triangular section. In addition, they may consist of eccentric conducting rods.

According to the realm of intervention in which the penetration instrument is used, the device may comprise at least one electrode at its distal end(s). The device may also comprise two electrodes arranged at the distal end of the penetration instrument, the electrodes consisting of conducting rods of concentric circular section.

The means of detection may consist of visual marking preferably on the handle of the exploration device. According to one specific means of creation of the device, the handle forms the means of detection.

The device may also comprise a central channel for the passage of an additional instrument.

Figure 1:
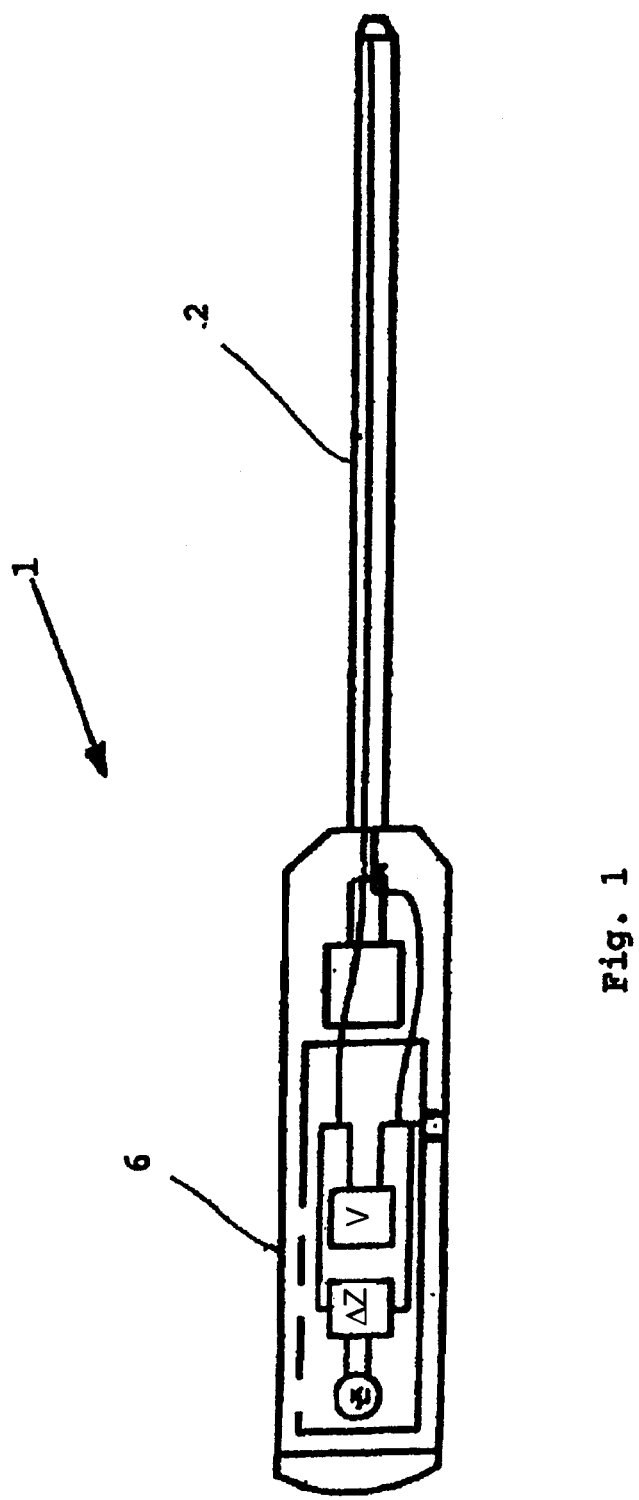
FIG. 1 is a diagram of an exploration device including a voltage source and an impedance measurer.

Turning now to the Drawings, the exploration device (1), illustrated in FIG. 1, is a device enabling the monitoring of the penetration of an instrument (2) in the bone structures of a human or animal body, the structures having at least two different zones of electrical impedance.

The exploration device (1) comprises a source of voltage supplying at least two electrodes and a means to measure the impedance between the electrodes.

At least one of the electrodes is found on the penetration instrument (2).

The device also comprises means for signalling producing a signal at the time of detection, by impedometer, a variation of impedance, and therefore the presence of a gap. The means for signalling includes emission of a visual signal, such as a light, a sound signal, and/or a tactile signal (vibrator, etc.).

The device may also comprise means for the acquisition and visualisation of the position of the gaps during penetration of the instrument (2) in the bone structure.

According to the applications considered, the penetration instrument (2) may either be fixed, or manually driven in rotation by means of drive of the motor type (not shown).

Therefore, it may include in one configuration, for example, of a probe, a square tip, a spatula, a curette or other, and in a second configuration, for example, of a screw, a drill, a tap, or other.

In the following section, the penetration instrument (2) includes a probe (2). However, the configurations presented are of course applicable to other penetration instruments mentioned above.

Figure 2:
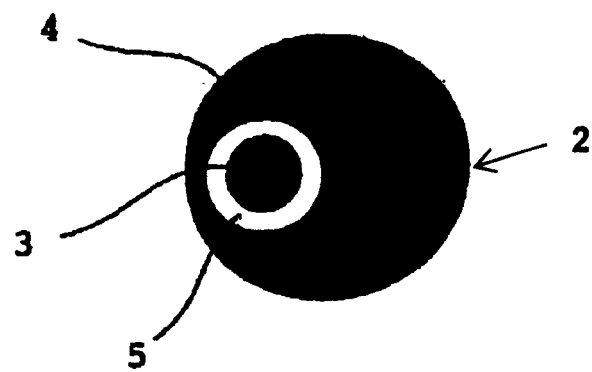
FIG. 2 is a front cutaway view of the distal end of the penetration instrument according to one configuration.

FIG. 2 illustrates one configuration of the probe (2) forming the exploration device (1).

In this configuration, the penetration instrument (2) has two eccentric electrodes (3, 4) of circular section at its distal end, electrode (3) being surrounded but separated from electrode (4) by an insulation ring (5).

In this example, electrode (3) comprises the positive pole of the electronic device, the negative pole of the electronic device comprising the electrode (4). This is only one example of an electronic device whose positive pole includes the electrode (4) and the negative pole of the electrode (3). Variations are within the skill in the art.

Each electrode (3, 4) is arranged to coincide with the surface of the penetration instrument (2).

To avoid any disturbance of the signal, the surface of the central or internal electrode (3) coinciding with the surface of the penetration instrument (2) remains relatively small with respect to the dimensions of the hole made in the bone cortex during the drilling (or other) operation.

The position of the electrode (3) is detected by specific marking on the exploration device (1). Advantageously, the marking is carried out by means of the handle (6) of the exploration device (1). It may, for example, include a visual signal, for example, an arrow, represented on the handle (6). The marking may also include any means directly on the handle (6), such as, for example, a specific shape of the handle (6).

Therefore, during penetration of the instrument (2) in the perforated bone structure, a signal is given off by the means for signalling when a variation in impedance measured between the electrodes (3, 4) is detected by the impedometer, indicating the presence of a gap.

Following such detection, the means for signalling emit a warning signal (visual, sound or tactile). The practitioner then knows that the electrode (3) from the penetration instrument is positioned in front of a gap.

The practitioner then determines the direction of the gap with the mark corresponding to the position of the electrode (3) marked on the handle (6) of the exploration device (1).

In order to enable full scanning of the bone structure, the penetration instrument (2) is endowed with a movement of rotation, the speed of rotation exceeding the speed of progress of the penetration instrument (2) in the bone structure. In other words, the speed of rotation of the instrument (2) is such that the aforementioned penetration instrument (2) sweeps at least 360 degrees by level of penetration.

Figure 3:
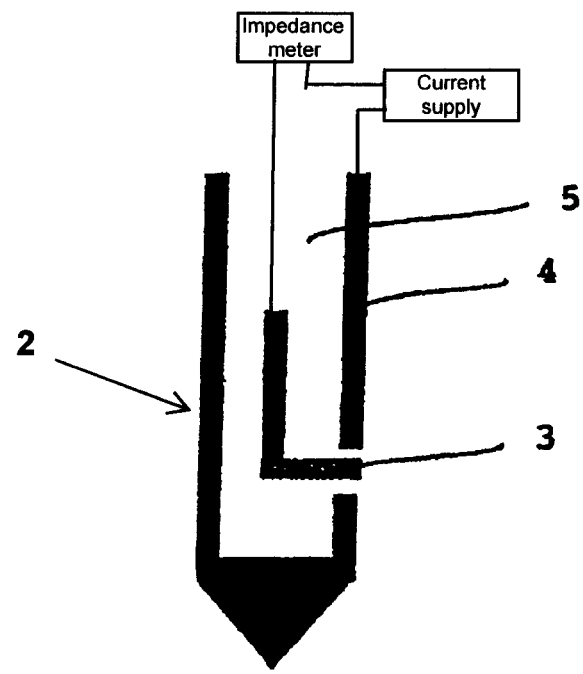
FIG. 3 is a longitudinal cutaway view of the penetration instrument according to another configuration.

FIG. 3 illustrates another configuration of the probe (2) comprising the exploration device (1), which enables detection of gaps laterally arranged with respect to the body of the penetration instrument (2).

In this configuration, the electrode (3) is positioned in the penetration instrument (2) to punctually coincide with the lateral surface of the penetration instrument (2).

As for the electrode (4), it is distributed on the rest of the lateral surface of the penetration instrument (2), including its distal end. The electrodes (3, 4) art separated from each other by an insulant (5).

The principle of detection and the determination of the direction of the gap are identical to that described above.

Figure 4:
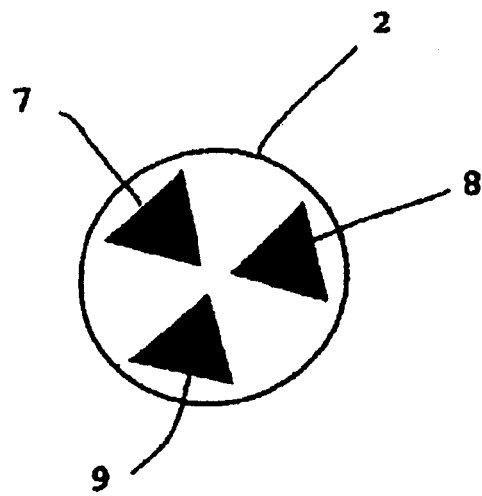
FIG. 4 is a front cutaway view of the distal end of the penetration instrument according to still another configuration.

FIG. 4 illustrates another configuration of the probe (2) comprising the exploration device (1), which enables detection of gaps arranged at the end of the penetration instrument (2).

In this configuration, the penetration instrument (2) has three electrodes (7, 8, 9) of sensibly identical triangular section at the distal end. The electrodes (7, 8, 9) distributed around the longitudinal axis of the penetration instrument (2) are angularly spaced. Advantageously, the angular space is identical.

Since the position of the electrodes (7, 8, 9) is known by the construction, their arrangement on the distal end provides indications about the position of the gaps. In fact, the gap detected will be located between the two electrodes for which a signal is emitted.

Since the number and triangular shape of the electrodes is given here by way of example, it is understood that the penetration instrument (2) may have a greater number of electrodes and a shape other than triangular. The determination of the direction of the gaps is all the more exact when the number of electrodes distributed at the end of the instrument (2) is higher.

Figure 5:
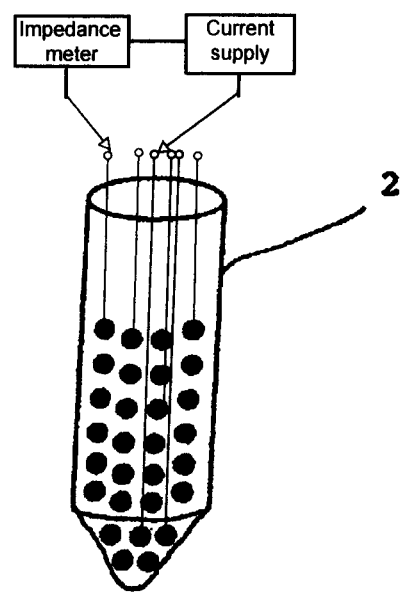
FIG. 5 is a perspective view of the penetration instrument according to yet another configuration.

FIG. 5 illustrates another configuration of the probe (2), enabling detection of the gaps arranged at the end of the penetration instrument (2), but also laterally.

In this configuration, the penetration instrument (2) includes a plurality of electrodes coinciding with the lateral surface of the penetration instrument (2) and at the distal end of the penetration instrument (2).

Since the position of each electrode is known, it is then possible to determine the position of the gap by the emission of a signal by the impedometer corresponding to the electrode positioned in front of the gap.

In the configurations presented above, the means to determine the position of the gaps include fixed electrodes. According to yet another configuration of the penetration instrument (2) (not shown), the gaps may also be determined by means of one or several mobile electrodes.

In addition, in the previous examples, the electrodes (3, 4) are respectively carried by the penetration instrument (2). Of course, the penetration instrument (2) may be equipped with only one electrode (3), the other electrode being positioned on the patient, and more specifically, on a surface other than the surgical wound, without going beyond the field of the invention.

As specified above, the configurations presented remain applicable to the other penetration instruments mentioned above.

Figure 6:
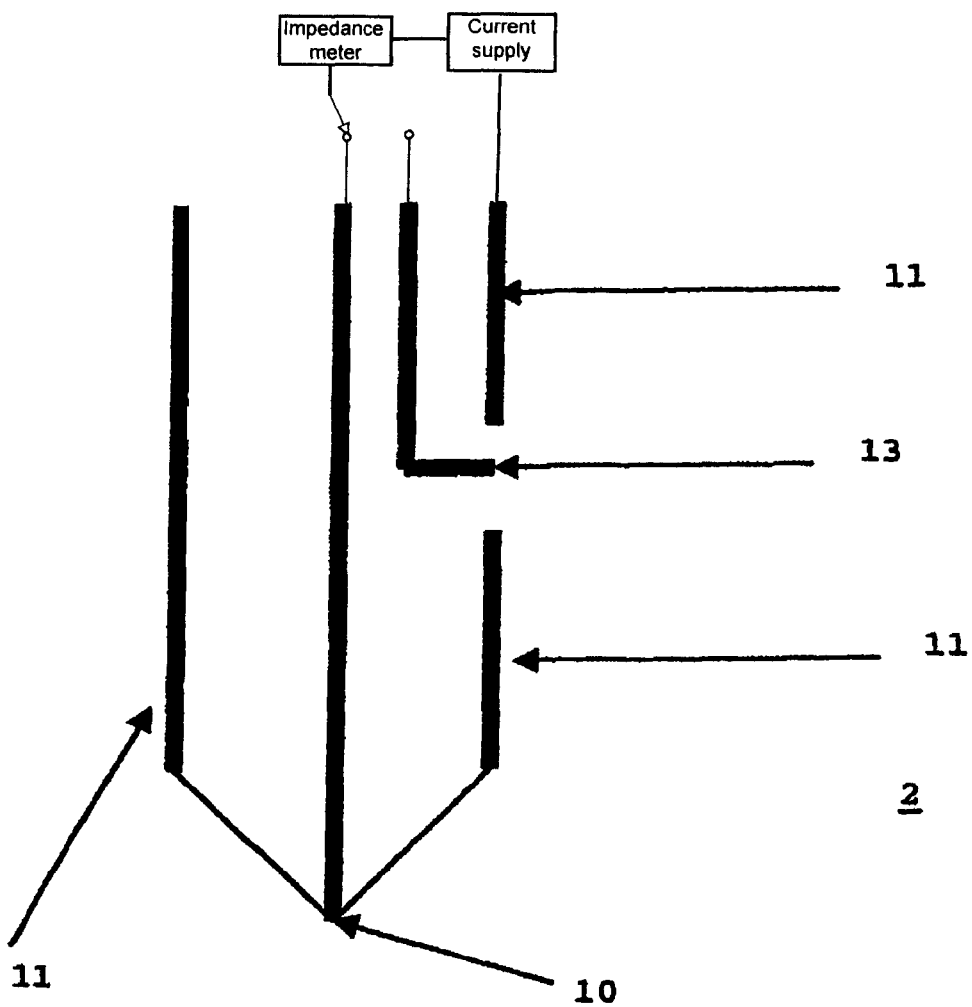
FIG. 6 is a longitudinal cutaway view of the penetration instrument according to a further configuration.

In particular, in the case where the penetration instrument (2) includes a drill element, the penetration instrument (2) may advantageously comprise at least one electrode (13) coinciding with the lateral surface of the penetration instrument (2), as well as two electrodes (10, 11) concentrically arranged at the distal end of the penetration instrument (2) (FIG. 6). It is therefore possible, due to the configuration of the penetration instrument (2) to determine the presence and direction of a gap by means of electrodes (11 and 13), as well as prevent any possible perforation of the bone cortex using electrodes (10 and 11). For this purpose, the positioning of a lateral electrode consisting of a rod extending to the distal end should be avoided. If fact, it would likely be impossible with such a configuration to know whether the zone detected by the electrodes is lateral or distal.

This disclosure is described above by way of example. It is understood that one skilled in the art is able to create different variations of the structures described and/or shown without departing from the subject matter recited in the appended claims.

The invention claimed is:

1. An exploration device to monitor the penetration of an instrument in an anatomic structure comprising:
   at least two electrodes;
   a source of voltage supplying the at least two electrodes;
   a means for measuring impedance of the anatomic structure between the electrodes;
   a means of angular location formed by at least one electrode punctually coinciding with a peripheral surface of the penetration instrument, the coinciding surface of the electrode having a position set off from a longitudinal axis the instrument; and
   means for detecting an angular position of the at least one electrode.

2. The exploration device according to claim 1, wherein the electrode punctually coincides with a lateral surface of the penetration instrument.

3. The exploration device according to claim 1, wherein the electrode punctually coincides with a peripheral surface of a distal end portion of the penetration instrument.

4. The exploration device according to claim 1, wherein the coinciding electrode is rotatably movable.

5. The exploration device according to claim 4, wherein the coinciding electrode is driven at a speed of rotation so that the electrode sweeps at least 360 degrees per level of drilling of the penetration instrument in the bone structure.

6. The exploration device according to claim 1, wherein the electrodes are a plurality of coinciding angularly spaced fixed electrodes and means for measuring impedance delivers a signal corresponding to each of the electrodes.

7. The exploration device according to claim 6, wherein the electrodes are longitudinally and angularly spaced punctual contacts.

8. The exploration device according to claim 6, wherein the electrodes are formed of longitudinal strips.

9. The exploration device according to claim 6, wherein the electrodes are distributed around the longitudinal axis of the penetration instrument.

10. The exploration device according to claim 6, wherein the electrodes are symmetrically arranged with respect to the longitudinal axis of the penetration instrument.

11. The exploration device according to claim 6, wherein the electrodes are conducing rods of circular, semi-annular, rectangular and/or triangular section.

12. The exploration device according to claim 6, wherein the electrodes are formed by eccentric conducing rods.

13. The exploration device according to claim 1, further comprising at least one electrode arranged at a distal end of the penetration instrument.

14. The exploration device according to claim 13, wherein two electrodes are arranged at the distal end of the penetration instrument, the electrodes consisting of conducting rods of substantially concentric circular section.

15. The exploration device according to claim 1, wherein the means for detecting comprises a visual marking on a handle of the exploration device.

16. The exploration device according to claim 1, further comprising a handle forming the means for detecting.

17. The exploration device according to claim 1, further comprising a central channel for passage of an additional instruments.

18. An exploration device to monitor the penetration of an instrument in an anatomic structure comprising:
    at least two electrodes;
    a source of voltage supplying the at least two electrodes;
    an impedance measuring device that measures impedance of the anatomic structure between the electrodes;
    an angular locator formed by at least one electrode punctually coinciding with a peripheral surface of the penetration instrument, the coinciding surface of the electrode having a position set off from a longitudinal axis the instrument; and
    a detector that detects an angular position of the at least one electrode.

19. The exploration device according to claim 18, wherein the at least one electrode is surrounded by an insulator and comprises an end that is locally flush with the peripheral surface of the instrument while being offset with respect to the longitudinal axis of the instrument.

* * * * *